US006930101B1

(12) United States Patent
Carson et al.

(10) Patent No.: US 6,930,101 B1
(45) Date of Patent: Aug. 16, 2005

(54) THIAZOLOPYRIMIDINES USEFUL AS TNFα INHIBITORS

(75) Inventors: Dennis A. Carson, Del Mar, CA (US); Howard B. Cottam, Escondido, CA (US); Lynn Deng, Grenanda Hills, CA (US)

(73) Assignee: The Regents of the University of California, Oakland, CA (US)

( * ) Notice: Subject to any disclaimer, the term of this patent is extended or adjusted under 35 U.S.C. 154(b) by 833 days.

(21) Appl. No.: 09/313,048

(22) Filed: May 17, 1999

(51) Int. Cl.[7] .................. C07D 513/04; A61K 31/519; A61P 11/06; A61P 19/02; A61P 37/06
(52) U.S. Cl. ...................... 514/81; 514/260.1; 544/255; 544/244
(58) Field of Search ...................... 514/258, 80, 260.1, 514/81; 544/280, 244, 255, 2

(56) References Cited

U.S. PATENT DOCUMENTS

| | | | |
|---|---|---|---|
| 3,127,402 A | 3/1964 | Pachter et al. | 260/251.5 |
| 3,594,378 A | 7/1971 | Laliberte et al. | 260/251 |
| 3,919,201 A | 11/1975 | Evans | 260/240 J |
| 4,041,167 A | 8/1977 | Moser et al. | 242/279 |
| 4,091,219 A | 5/1978 | Denzel et al. | 544/117 |
| 4,103,016 A | 7/1978 | Moser et al. | 424/270 |
| 4,110,451 A | 8/1978 | Moser et al. | 424/251 |
| 4,111,693 A | 9/1978 | Wright et al. | 96/1.6 |
| 4,160,768 A | 7/1979 | Moser et al. | 260/306.7 T |
| 4,175,961 A | 11/1979 | Wright et al. | 430/58 |
| 4,224,334 A | 9/1980 | Moser et al. | 424/270 |
| 4,510,141 A | 4/1985 | Heckendorn | 514/250 |
| 4,593,095 A | 6/1986 | Snyder et al. | 544/272 |
| 4,665,182 A | 5/1987 | Nichol et al. | 544/258 |
| 4,701,455 A | 10/1987 | Nichol et al. | 514/249 |
| 4,766,133 A | 8/1988 | Fischli et al. | 514/338 |
| 4,769,377 A | 9/1988 | Snyder et al. | 514/263 |
| 4,778,806 A | 10/1988 | Bender et al. | 514/336 |
| 4,794,114 A | 12/1988 | Bender et al. | 514/333 |
| 4,931,437 A | 6/1990 | Fedi et al. | 514/234.2 |
| 4,996,208 A | 2/1991 | Lindner et al. | 514/258 |
| 5,198,547 A | 3/1993 | Bailey et al. | 544/258 |
| 5,288,721 A | 2/1994 | Klein et al. | 514/263 |
| 5,294,612 A | 3/1994 | Bacon et al. | 514/234.2 |
| 5,317,019 A | 5/1994 | Bender et al. | 514/224.2 |
| 5,366,978 A | 11/1994 | Furukawa et al. | 514/263 |
| 5,424,311 A | 6/1995 | Billhardt-Troughton et al. | 514/248 |
| 5,521,181 A | 5/1996 | Meyer et al. | 514/249 |
| 5,593,992 A | 1/1997 | Adams et al. | 514/235.8 |
| 5,599,813 A | 2/1997 | Matsumoto et al. | 514/232.5 |
| 5,656,644 A | 8/1997 | Adams et al. | 514/341 |
| 5,658,903 A | 8/1997 | Adams et al. | 514/253.8 |
| 5,670,506 A | 9/1997 | Leigh et al. | 514/258 |
| 5,750,575 A | 5/1998 | Klein et al. | 514/617 |
| 5,792,767 A | 8/1998 | Meyer et al. | 514/249 |
| 5,843,943 A | 12/1998 | Carson et al. | 514/249 |
| 5,877,180 A | 3/1999 | Linden et al. | 514/266 |
| 2004/0038994 A1 * | 2/2004 | Wilson | 514/260.1 |

FOREIGN PATENT DOCUMENTS

| | | | |
|---|---|---|---|
| DE | 2038922 | 3/1971 | |
| EP | 0188150 | 7/1986 | |
| EP | 0348746 | 1/1990 | |
| EP | 0490181 | 6/1992 | |
| EP | 0493682 | 7/1992 | |
| EP | 0733633 | 9/1996 | |
| EP | 0849256 | 6/1998 | |
| JP | 08-092250 | 4/1996 | |
| WO | 92/10190 | 6/1992 | |
| WO | 92/21344 | 12/1992 | |
| WO | 93/06090 | 4/1993 | |
| WO | 93/16699 | 9/1993 | .......... A61K/31/52 |
| WO | 96/40143 | 12/1996 | |
| WO | 97/25045 | 7/1997 | |
| WO | 97/25047 | 7/1997 | |
| WO | 97/25048 | 7/1997 | |
| WO | 98/22464 | 5/1998 | ......... C07D/473/06 |
| WO | 98/52948 | 11/1998 | |

OTHER PUBLICATIONS

Benjamin K. Gill, "Diagram Representing the Roles of Cytokines in Inflammatory Responses" http://attila.stevens-tech.edu/chembio/bgill/L10K.html downloaded from the Internet Aug. 12, 2002.*

Goncalves de Morales et al. Effects of cyclo–oxygenase inhibitors and modulators of cyclic AMP formation on lipopolysaccharide–induced neutrophil infiltration in mouse lung. J. of Pharm. 117, pp. 1792–1796, 1996.*

Chemical Abstracts, vol. 69, 36067 (1968).

Chemical Abstracts, vol. 72, 12658 (1970).

Abdel–Fattah, A.M., et al., "Reactions with 6–Methyl–2–Thiouracil Synthesis of Dipyrimidino[2, 1–b:1', 2' –c]Thiazine. A New Ring System", *Phosphorus, Sulfur, and Silicon*, 72, pp. 145–156, (1992).

Basyouni, W.M., et al., "Synthesis and Molluscicidal Properties of Some Newer Thiazoles and Their Thiazolo [5,4, –d] Pyrimidinone Derivatives", *Egypt. J. Bilh.*, 17, pp. 91–102, (1995).

Bruns, R.F., "Adenosine Antagonism by Purines, Pteridines and Benzopteridines in Human Fibroblasts", *Biochemical Pharmacology*, 30, pp. 325–333, (1981).

Flammang, R., et al., "Iminoethenethiones, RN==C==C==S: Characterization by Neutralization–Reionization Mass Spectrometry and G2(MP2) Theory", *Journal of the American Chemical Society*, 116 (5), pp. 2005–2013, (1994).

Furrer, H., et al., "A new class of potent hypolipemic agents raising high–density lipoproteins. Synthesis, reactions and pharmacological properties", *Eur. J. Med. Chem.*, 29, pp. 819–829, (1994).

(Continued)

*Primary Examiner*—Mark L. Berch
(74) *Attorney, Agent, or Firm*—Schwegman, Lundberg, Woessner & Kluth, P.A.

(57) ABSTRACT

The invention provides derivatives of thiazolo[4,5-dl] pyrimidine and their use as inhibitors of proinflammatory cytokines.

12 Claims, 7 Drawing Sheets

OTHER PUBLICATIONS

Ghoneim, K.M., et al., "Study on the Formation of Thiazolopyrimidinediones and Pyrimidothiazinediones from 6–Methyl–2–thiouracil", *Polich. J. Chem.*, 72, pp. 1173–1177, (1997).

Glennon, R.A., et al., "Alkylation Studies on 6–Ethyl–2, 3–dihydrothiazolo–[3,2–α] pyrimidine–5,7–diones", *Journal of Heterocyclic Chemistry*, 16 (5), pp. 903–907, (Jul. 1979).

Goldman, I.M., "A Novel Thiazole Synthesis.4,5,6,7–Tetrahydrothiazolo[4,5–d]pyrimidine–5,7–diones", *The Journal of Organic Chemistry*, 34 (11), pp. 3285–3289, (Nov. 1969).

Grohe, K., et al., "Cycloacylierung von Enaminen, I Synthese von 2–Thiazolon–Derivaten", *Liebigs Ann. Chem.*, pp. 1018–1024, (1973).

Itoh, T., et al., "Synthesis of Some Tricyclic Heterocycles from 5,6–Diamino–1,3–dimethyluracil", *Chem. Pharm. Bull.*, 37 (8), pp. 2197–2199, (Aug. 1989).

Kaul, R., et al., "2–$^{14}$C–1–Allyl–3,5–diethyl–6–chlorouracil II: Isolation and Structures of the Major Sulfur–Free and Three Minor Sulfur–Containing Metabolites and Mechanism of Biotransformation", *Journal of Pharmaceutical Sciences*, 71 (8), pp. 897–900, (Aug. 1982).

Kaul, R., et al., "Mechanism of Formation of SCH$_3$–Metabolites Investigated on the Biotransformation of 1–Allyl–3, 5–Diethyl–6–Chlorouracil in Rabbits", *Chemopshere*, 10 (8), pp. 929–934, (1981).

Komoriya, K., et al., "Characterization of Immunomodulating Action of TI–31 on Antibody Response in Mice", *J. Pharmacobio–Dyn.*, 14, pp. 443–447, (1991).

Lewis, A.F., et al., "Thiazolo[4,5–d]pyrimidines. Part I. Synthesis and Anti Human Cytomegalovirus (HCMV) Activity in vitro of Certain Alkyl Derivatives", *J. Heterocyclic Chem.*, 32, pp. 547–556, (Mar.–Apr. 1995).

Mbagwu, G.O., et al., "Carbon–13 Nuclear Magnetic Resonance Spectra of Some Mesoionic Xanthine Analogs", *Organic Magnetic Resonance*, 21 (9), pp. 527–531, (1983).

Mbagwu, G. O., "Studies of Amine–Induced Ring Opening of Some Mesoionic Xanthines", *J. Heterocyclic Chem.*, 22, pp. 465–474, (1985).

Mizuno, Y., et al., "Synthesis of a Potential Antitumor Agent: 4–(β–D–Ribofuransoyl)—4,5,6,7–tetrahydrothiazolo[4,5–d]pyrimidine–5,7–dione (Thioanalog of 3–Isoxanthosine)", *Chem. Pharm. Bull.*, 22 (5), pp. 1198–1200, (1974).

Nagahara, K., et al., "Thiazolo[4 5–d]pyrimidine Nucleosides. The Synthesis of Certain 3–β–D–Ribofuranosylthiazolo[4,5–d]pyrimidines ad Potential Immunotherapeutic Agents", *J. Med. Chem.*, 33, pp. 407–415, (1990).

Sen, D., et al., "Effect of Mesoionic Xanthine Analogs on *Trypanosoma musculi* Development in Mice", *J. Euk. Microl.*, 40 (3), pp. 259–262, (1993).

Sudhakar Rao, T., et al., "Synthesis of 4,6–Disubstituted–7–β–D–ribofuranosyl– and Arabinofuranosylpyrazolo[3,4–d]pyrimidines and Cetain Related Ribonucleosides", *J. Heterocyclic Chem.*, 28, pp. 1779–1788, (1991).

Szajda, M., et al., "Reactions of 2–Thiothymine with Esters of Chloroacetic Acid", *Polish Journal of Chemistry*, 52, pp. 1027–1031, (1983).

Takahashi, H., et al., "A One–Step Synthesis of Glycosylaminoisothiazolo[3,4–d] pyrimidines and Glycosylaminoisothiazoles", *Chem. Pharm. Bull.*, 27(5), pp. 1147–1152, (1979).

In: *Remington's Pharmaceutical Sciences, Eighteenth Edition*, Gennaro, A.R., (ed.), Mack Publishing Company, Easton, PA, p. 391 (1990).

In: *Remington's Pharmaceutical Sciences, Eighteenth Edition*, Gennaro, A.R., (ed.), Mack Publishing Company, Easton, PA, p. 1115–1121, (1990).

Badger, A.M., et al., "Pharmacological Profile of SB 203580, a Selective Inhibitor of Cytokine Suppressive Binding Protein/p38 Kinase, in Animal Models of Arthritis, Bone Resorption, Endotoxin Shock and Immune Function", *The Journal of Pharmacology and Experimental Therapeutics*, 279, 1453–1461, (1996).

Baker, J.A., et al., "Synthesis of Derivatives of Thizolo[4, 5–d]pyrimidine. Part II", *Journal of the Chemical Society(C)*, 18, 2478–2484, (1970).

Boehm, J.C., et al., "1–Substituted 4–Aryl–5–pyridinylimidazoles: A New Class of Cytokine Suppressive Drugs with Low 5–Lipoxygenase and Cyclooxygenase Inhibitory Potency", *Journal of Medical Chemistry*, 39, 3929–3937, (1996).

Boujrad, N., et al., "Inhibition of Hormones–Stimulated Steroidogenesis in Cultured Leydig Tumor Cells by a Cholesterol–Linked Phosphorothioate Oligodeoxynucleotide Antisense to Diazepam–Binding Inhibitor", *Proc. Natl. Acad. Sci. USA*, 90, 5728–5731, (Jun. 1993).

Burrows, J.L., "Determination of Oxpentifylline and Three Metabolites in Plasma by Automted Capillary Gas Chromatography using Nitrogen–Selective Detection", *Journal of Chromatography*, 423, 139–146, (1987).

Cembrzynska–Nowak, M., et al., "Elevated Release of Tumor Necrosis Factor–alpha and Interferon–gamma by Bronchoalveolar Leukocytes from Patients with Bronchial Asthma", *American Review of Respiratory Diseases*, 147, 291–295, (1993).

Chaby, R., "Strategies for the Control of LPS–Mediated Pathophysiological Disorders", *Drug Discovery Today*, 4, 209–221, (May 1999).

Chaudhri, G., et al., "Reactive Oxygen Species Facilitate in vitro and in vivo Lipopolysaccharide–Induced Release of Tumor Necrosis Factor", *The Journal of Immunology*, 143, 1290–1294, (Aug. 15, 1989).

Cifone, M.G., et al., "Apoptotic Signalling through CD95 (FAS/Apo–1) Activates an Acidic Sphingomyelinase", *The Journal of Experimental Medicine*, 177, 1547–1552, (Oct. 1993).

Cottam, H.B., et al., "Substituted Xanthines, Pteridinediones, and Related Compunds as Potential Antiinflammatory Agents. Synthesis and Biological Evaluation of Inhibitors of Tumor Necrosis Factor α", *Journal of Medicinal Chemistry*, 39, 2–9, (1996).

Coughlan, A.F., et al., "P–Selectin and Platelet–activating Factor Mediate Initial Endotoxin–induced Neutropenia", *The Journal of Experimental Medicine*, 179, 329–334, (Jan. 1994).

Crouch, S.P., et al., "Effect of Ingested Pentoxifylline on Neutrophil Superoxide Anion Production", *Infection and Immunity*, 60, 4504–4509, (Nov. 1992).

Curran, W.V., et al., "Pteridine Chemistry. VII. The Cyanoethylation of Some Hydroxypteridines", *Chemical Abstracts*, 57, As Reported by Smith, M.E., 5920–5922, (1962).

Day, C.P., et al., "Plasma Membrane Form of Phosphatidate Phosphohydrolase: a Possible Role in Signal Transduction During Liver Fibrogenesis", *Clinical Science*, 85, 281–287, (1993).

Dbaibo, G.S., et al., "Tumor Necrosis Factor–α (TNF–α) Signal Transduction through Ceramide", *The Journal of Biological Chemistry*, 268, 17762–17766, (Aug. 25, 1993).

Dinarello, C.A., "Interleukin–1 and Tumor Necrosis Factor: Effector Cytokines in Autoimmune Diseases", *Seminars in Immunology*, 4, 133–145 (1992).

Dressler, K.A., et al., "Tumor Necrosis Factor–α Activates the Sphinomyelin Siganl Transduction Pathway in a Cell–Free System", *Science*, 225, 1715–1718, (Mar. 27, 1992).

Gallagher, T.F., et al., "2,4,5–Triarylimidazole Inhibitors of IL–1 Biosynthesis", *Bioorganic&Medicinal Chemistry Letters*, 5, 1171–1176, (1995).

Grabarek, Z., et al., "Zero–Length Crosslinking Procedure with the Use of Active Esters", *Analytical Biochemistry*, 185, 131–135, (1990).

Griswold, D.E., et al., "Differentiation in vivo of Classical Non–Steroidal Antiinflammatory Drugs from Cytokine Suppressive Antiinflammatory Drugs and Other Pharmacological Classes Using Mouse Tumour Necrosis Factor alpha Production", *Drugs Under Experimental and Clinical Research*, XIX, 243–248, (1993).

Griswold, D.E., et al., "Evaluation of Human Cytokine Production and Effects of Pharmacological Agents in a Heterologous System in Vivo", *Journal of Immunological Methods*, 195, 1–5, (1996).

Haimovitz–Friedman, A., et al., "Ionizing Radiation Acts on Cellular Membranes to Generate Ceramide and Initiate Apoptosis", *The Journal of Experimental Medicine*, 180, 525–535, (Aug. 1994).

Han, H., et al., "5'–Amino Acid Esters of Antiviral Nucleosides, Acyclovir, and AZT are Absorbed by the Intestinal PEPT1 Peptide Transporter", *Phamaceutical Research*, 15, 1154–1159, (1998).

Hannun, Y.A., et al., "Ceramide: An Intracellular Signal for Apoptosis", *TIBS*, 20, 73–77, (Feb. 1995).

Hotamisligil, G.S., et al., "Adipose Expression of Tumor Necrosis Factor–α: Direct Role in Obesity–Linked Insulin Resistance", *Science*, 259, 87–91, (Jan. 1, 1993).

Imagawa, D.K., et al., "The Role of Tumor Necrosis Factor in Allograft Rejection", *Transplantation*, 51, 57–62, (Jan. 1991).

Jacobs, L.S., et al., "Sphingolipids as Mediators of Effects of Platelet–Derived Growth Factor in Vascular Smooth Muscle Cells", *American Journal of Physiology*, 265, C740–C747, (Sep. 1993).

Jayadev, S., et al., "Role for Ceramide in Cell Cycle Arrest", *The Journal of Biological Chemistry*, 270, 2047–2052, (Feb. 3, 1995).

Joseph, C.K., et al., "Bacterial Lipopolysaccharide Has Structural Similarity to Cermaide and Stimulates Ceramide–activated Protein Kinase in Myeloid Cells", *The Journal of Biological Chemistry*, 269, 17606–17610, (Jul. 1, 1994).

Klein, R.S., et al., "New Synthesis of 5 H–Pyrrolo[3,2–d] pyrimidines via Pyrimido [5,4–c] Pyridazines", *Journal of Organic Chemistry*, 43, 2536–2539, (1978).

Kumar, S., et al., "Novel Homologues of CSBP/p38 MAP Kinase: Activation, Substrate Specificity and Sensitivity to Inhibition by Pyridinyl Imidozoles", *Biochemical and Biophysical Research Communications*, 235, 533–538, (1997).

Kurimoto, I., et al., "cis–Urocanic Acid Suppression of Contact Hypersensitivity Induction is Mediated Via Tumor Necrosis Factor–α", *The Journal of Immunology*, 148, 3072–3078, (May 15, 1992).

Legrand–Poels, S., et al., "Activation of Human Immunodeficiency Virus Type I by Oxidative Stress", *AIDS Research and Human Retroviruses*, 6, 1389–1397, (1990).

Lister, J.H., et al., In: *Fused Pyrimidines—Part II: Purines*, Brown, D.J., (series ed.), John Wiley & Sons, Inc., New York, p. 31–90, (1971).

Lister, J.H., et al., In: *Fused Pyrimidines—Part II: Purines*, Brown, D.J., (series ed.), John Wiley & Sons, Inc., New York, p. 220, (1971).

Liu, J., et al., "Renaturation and Tumor Necrosis Factor–α Stimulation of a 97–kDa Ceramide–activated Protein Kinase", *The Journal of Biological Chemistry*, 269, 3047–3052, (Jan. 28, 1994).

Liu, M.K., et al., "CD14–Dependent Activation of Protein Kinase C and Mitogen–Activated Protein Kinase (p42 and p44) in Human Monocytes Treated with Bacterial Lipopolysaccharide", *The Journal of Immunology*, 153, 2642–2652, (1994).

Lømo, J., et al., "TGF–β1 and Cyclic AMP Promote Apoptosis in Resting Human B Lymphocytes", *The Journal of Immunology*, 154, 1634–1643, (1995).

Lozano, J., et al., "Protein Kinase C ζIsoform Is Critical for $^k$B–dependent Promoter Activation by Sphingomyelinase", *The Journal of Biological Chemistry*, 269, 19200–19202, (1994).

Männel, D.N., et al., "Tumor Necrosis Factor: A Cytokine Involved in Toxic Effects of Endotoxin", *Reviews of Infectious Diseases*, 9, S602–S606, (1987).

Marshall, P.J., et al., "Pharmacology of the Pyrroliomidazole, SK&F 105809–I", *Biochemical Pharmacology*, 42, 813–824, (1991).

Mathias, S., et al., "Activation of the Sphingomyelin Signaling Pathway in Intact EL4 Cells and in Cell–Free System by IL–1 β", *Science*, 259, 519–522, (Jan. 22, 1993).

Matsuyama, T., et al., "Cytokines and HIV Infection: is AIDS a Tumor Necrosis Factor Disease?", *AIDS*, 5, 1405–1417, (1991).

Meskini, N., et al., "Phosphodiesterase Inhibitory Profile of Some Related Xanthine Derivatives Pharmacologically Active on the Peripheral Microcirculation", *Biochemical Pharmacology*, 47, 781–788, (1994).

Moreira, R., et al., "A New Direct Synthesis of Tertiary N–Acyloxymethylamide Prodrugs of Carboxylic Acid Drugs", *Tetrahedron Letters*, 35, 7107–7110, (1994).

Moreira, R., et al., "Acyloxymethyl as a Drug Protecting Group. Part 3. Tertiary O–Amidomethyl Esters of Penicillan G: Chemical Hydrolysis and Anti–Bacterial Activity", *Pharmaceutical Research*, 13, 70–75, (1996).

Nishigaki, S., et al., "New Synthesis of a Pteridine", *Heterocyles*, 15, 757–759, (1981).

Opal, S.M., et al., "Clinical Trials for Severe Sepsis", *Infectious Disease Clinics of North America*, 13, 285–297, (Jun. 1999).

Peterson, T.C., "Pentoxifylline Prevents Fibrosis in an Animal Model and Inhibits Platelet–derived Growth Factor–driven Proliferation of Fibroblasts", *Hepatology, 17*, 486–493, (1993).

Raines, M.A., et al., "Sphingomyelinase and Ceramide Activate Mitogen–Activated Protein Kinase in Myeloid HL–60 Cells", *The Journal of Biological Chemistry, 268*, 14572–14575, (Jul. 15, 1993).

Rice, G.C., et al., "Protection from Endotoxic Shock in Mice by Pharmacologic Inhibition of Phosphatidic Acid", *Proc. Natl. Acad. Sci. USA, 91*, 3857–3861, (Apr. 1994).

Ridley, S.H., et al., "Actions of IL–1 are Selectively Controlled by p38 Mitogen–Activated Protein Kinase", *The Journal of Immunology, 158*, 3165–3173, (1997).

Rivas, C.I., et al., "Involvement of the Sphingomyelin Pathway in Autocrine Tumor Necrosis Factor Signalling for Human Immunodeficiency Virus Production in Chronically Infected HL–60 Cells", *Blood, 83*, 2191–2197, (Apr. 15, 1994).

Schrage, A., et al., "Studies on Condensed Pyrimidine Systems. V. (1) The Pyrimido [4,5–c] [1,2,5] thiadiazole Ring Systems", *Journal of Organic Chemistry, 16*, 207–215, (1951).

Seekamp, A., et al., "Ischemia—Reperfusion Injury", *Agents and Actions Supplements, 41*, 137–152, (1993).

Semmler, J., et al., "Xanthine Derivatives: Comparison between Suppression of Tumor Necrosis Factor–$\alpha$ Production and Inhibition of cAMP Phosphodiesterase Activity", *Immunology, 78*, 520–525, (1993).

Sharief, M.K., et al., "Elevated Serum Levels of Tumor Necrosis Factor–$\alpha$ in Guillain–Barré Syndrome", *Annals of Neurology, 33*, 591–596, (Jun. 1993).

Sliwa, K., et al., "Randomized Investigation of Effects of Pentoxifylline on Left–Ventricular Perfomance in Idiopathic Dilated Cardiomyopathy", *The Lancet, 351*, 1091–1093, (Apr. 11, 1998).

Staros, J.V., et al., "Enhancement by N–Hydroxysulfosuccinimade of Water–Soluble Carbodiimide–Mediated Coupling Reactions", *Analytical Biochemistry, 156*, 220–222, (1986).

Strieter, R.M., et al., "Cellular and Molecular Regulation of Tumor Necrosis Factor–alpha Production by Pentoxifylline", *Biochemical and Biophysical Research Communications, 155*, 1230–1236, (Sep. 30, 1988).

Timmis, G.M., "A New Synthesis of Pteridines", *Nature, 164*, 139, (Jul. 23, 1949).

Tracey, K.J., et al., "Cachectin/Tumor Necrosis Factor Induces Cachexia, Anemia, and Inflammation", *Journal of Experimental Medicine, 167*, 1211–1227, (Mar. 1988).

Venable, M.E., et al., "Identification of a Defect in the Phospholipase D/Diacylglycerol Pathway in Cellular Senescence", *The Journal of Biological Chemistry, 269*, 26040–26044, (Oct. 21, 1994).

Verheij, M., et al., "Requirement for Ceramide–Initiated SAPK/JNK Signalling in Stress–Induced Apoptosis", *Nature, 380*, 75–79, (Mar. 7, 1996).

Ward, A., et al., "Pentoxifylline—A Review of its Pharmacodynamic and Pharmacokinetic Properties, and its Therapeutic Efficacy", *Drugs, 34*, 50–97, (1987).

Wilson, K.P., et al., "The Structural Basis for the Specificity of Pyridinylimidazole Inhibitors of p38 MAP Kinase", *Chemistry& Biology, 4*, 423–431, (Jun. 1997).

Wolff, R.A., et al., "Role of Ceramide–activated Protein Phosphatase in Ceramide–mediated Signal Transduction", *The Journal of Biological Chemistry, 269*, 19605–19609, (Jul. 29, 1994).

Wu, J., et al., "Inhibition of the EGF–Activated MAP Kinase Signalling Pathway by Adenosine 3', 5' Monophosphate", *Science, 262*, 1065–1069, (Nov. 12, 1993).

Yanagawa, H., et al., "Analysis of Superhelical Structures of Nucleic Acid–Lipid Conjugates by Image Processing", *Nucleic Acids Research, Symposium Series No. 19*, Symposium on Nucleic Acids Technology, Okayama, Japan, 189–192, (Feb. 20–21, 1988).

* cited by examiner

THIAZOLOPYRIMIDINES USEFUL AS TNFα INHIBITORS (This invention was made with the support of NIH Grant No. BM23200. The Government has certain rights in the invention.)

BACKGROUND OF THE INVENTION

The release of inflammatory cytokines such as IL-1 and tumor necrosis factor-alpha (TNFα) by leukocytes is a means by which the immune system combats pathogenic invasions, including infections. TNFα stimulates the expression and activity of adherence factors on leukocytes and endothelial cells, primes neutrophils for an enhanced inflammatory response to secondary stimuli and enhances adherent neutrophil oxidative activity. See, Sharma et al., Med. of Inflamm., 6, 175 (1987). In addition, macrophages/dendritic cells act as accessory cells processing antigen for presentation to lymphocytes. The lymphocytes, in turn, become stimulated to act as pro-inflammatory cytotoxic cells.

Generally, cytokines stimulate neutrophils to enhance oxidative (e.g., superoxide and secondary products) and nonoxidative (e.g., myeloperoxidase and other enzymes) inflammatory activity. Inappropriate and over-release of cytokines can produce counterproductive exaggerated pathogenic effects through the release of tissue-damaging oxidative and nonoxidative products (K. G. Tracey et al., J. Exp. Med., 167, 1211 (1988); and D. N. Männel et al., Rev. Infect, Dis., 2 (suppl. 5), S602–S606 (1987)). For example, TNFα can induce neutrophils to adhere to the blood vessel wall and then to migrate through the tissue to the site of injury and release their oxidative and non-oxidative inflammatory products.

Although monocytes collect slowly at inflammatory foci, given favorable conditions, the monocytes develop into long-term resident accessory cells and macrophages. Upon stimulation with an inflammation trigger, monocytes/macrophages also produce and secrete an array of cytokines (including TNFα), complement, lipids, reactive oxygen species, proteases and growth factors that remodel tissue and regulate surrounding tissue functions.

Inflammatory cytokines have been shown to be pathogenic in: arthritis (C. A. Dinarello, Semin. Immunol., 4, 133 (1992)); ischemia (A. Seekamp et al., Agents-Actions-Supp., 41, 137 (1993)); septic shock (D. N. Männel et al., Rev. Infect. Dis., 9 (suppl. 5), S602–S606 (1987)); asthma (N. M. Cembrzynska et al., Am. Rev. Respir. Dis., 147, 291 (1993)); organ transplant rejection (D. K. Imagawa et al., Transplantation, 51, 57 (1991); multiple sclerosis (H. P. Hartung, Ann. Neurol., 33, 591 (1993)); and AIDS (T. Matsuyama et al., AIDS, 5, 1405 (1991)). In addition, superoxide formation in leukocytes has been implicated in promoting replication of the human immunodeficiency virus (HIV) (S. Legrand-Poels et al., AIDS Res. Hum. Retroviruses, 6, 1389 (1990)).

A series of substituted xanthine-like compounds including pteridinediones, quinazolinones, and isoquinolones have been reported which inhibit the production or action of TNFα in human monocytes stimulated with lipopolysaccharide (LPS) in vitro. See, for example, H. B. Cottam et al., J. Med. Chem., 3, 2 (1996) and D. Carson et al. (U.S. Pat. No. 5,843,943). The most active compounds of these series were found to be in the pteridinedione class and their activity was independent of phosphodiesterase inhibition. Moreover, these compounds bind only very weakly at adenosine receptors $A_1$ and $A_2$, and therefore elevations in intracellular cyclic AMP levels are unlikely to play a significant role in their biological activity.

However, a continuing need exists for compounds which can block the deleterious effects of the cytokine-mediated mammalian inflammatory response.

SUMMARY OF THE INVENTION

The present invention provides thiazolopyrimidines of formula (1):

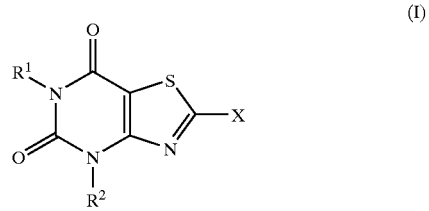

wherein $R^1$ is -Z-A wherein Z is (a) $C_1$–$C_7$ alkyl, optionally comprising 1–2 double bonds, 1–2 nonperoxide O or 1–2 NR wherein R is individually H, phenyl, $C_2$–$C_4$ alkanoyl, benzyl or $C_1$–$C_6$ alkyl; (b) $C_3$–$C_6$ cycloalkyl; (c) $C_3$–$C_6$ cycloalkyl $C_1$–$C_3$ alkyl; (d) $C_6$–$C_{10}$ aryl; or (e) $C_6$–$C_{10}$ aryl $C_1$–$C_3$ alkyl;

A is $N(R)_2$, $C_2$–$C_4$ acyloxy, $SO_3H$, $PO_4H_2$, $N(NO)(OH)$, $SO_2NH_2$, $PO(OH)NH_2$, OH, $SO_2R^3$, tetrazolyl, or $COOR^3$, wherein $R^3$ is H, phenyl, benzyl or $C_1$–$C_6$ alkyl optionally substituted with 1–2 OR, $C_6$–$C_{10}$ heteroaryl, $C_6$–$C_{10}$ aryl, $C_2$–$C_4$ alkenyl, phenyl, tetrazolyl or OY wherein Y an ester of an amino acid;

$R^2$ is a $C_1$–$C_6$ alkyl, $C_2$–$C_4$ alkenyl, $C_6$–$C_{10}$ aryl $C_1$–$C_2$ alkyl or $C_6$–$C_{10}$ heteroaryl $C_1$–$C_2$ alkyl;

X is H, halo, OR, SR, $N_3$ or $N(R)_2$; or a pharmaceutically acceptable salt thereof.

Preferably, $R^1$ is —$(CH_2)_nA$ wherein n is 2–6, wherein 1–2 $CH_2$ can optionally be replaced by 1–2 nonperoxide O or NH; or $R^1$ is phenyl substituted with A, i.e., 4-A-phenyl; A is preferably $CO_2R$; X preferably is $N(R)_2$ wherein each R is individually H, $(C_1$–$C_4)$alkyl, $C_2$–$C_4$ alkanoyl, or phenyl; preferably, H or $CH_3$.

These compounds are derivatives of the thiazolo[4,5-d] pyrimidine ring system and are also xanthine-like. When compared to the compounds of U.S. Pat. No. 5,843,943, the compounds of formula I can exhibit a 10- to 20-fold increase in potency as anti-TNFα agents. Thus, in vitro studies indicate $IC_{50}$ values of less than 500 nM for certain compounds of formula I. In vivo experiments in mice show certain of these compounds to have oral activity in a model of acute inflammation, while not exhibiting significant toxicity.

Compounds of formula (I) are inhibitors of TNFα release and can be useful to treat those diseases where overproduction of proinflammatory cytokines has been shown to play a major role. These may include autoimmune diseases such as rheumatoid arthritis, multiple sclerosis, asthma, psoriasis and inflammatory bowel disease. Other conditions, such as cardiomyopathy and congestive heart failure, and insulin-resistant diabetes, can also be treated using the present compounds.

Certain of the compounds of formula (I) are useful as intermediates in the preparation of other compounds of formula (1), e.g., as depicted below.

DETAILED DESCRIPTION OF THE INVENTION

Figure 1:
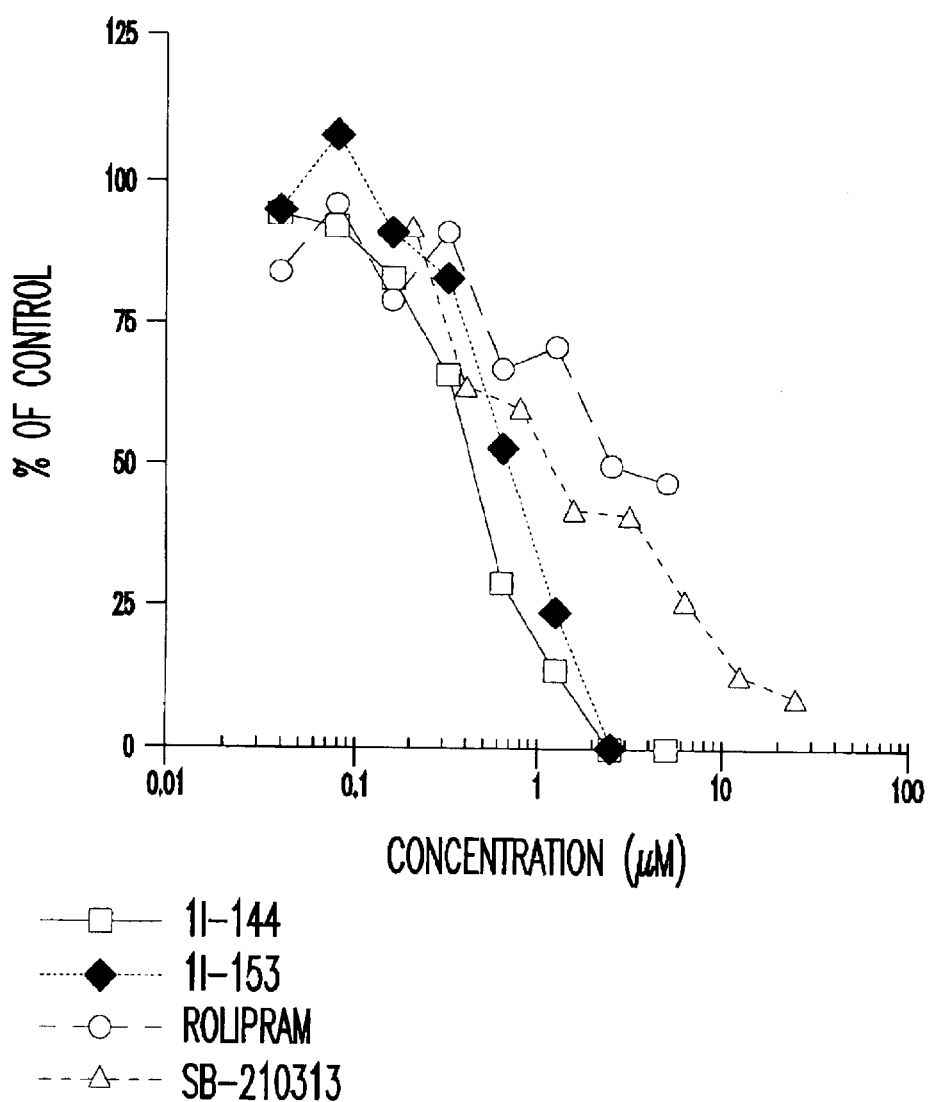
FIG. 1 is a graph depicting the effect of compounds of the invention on TNFα production in human monocytes using ELISA.

The following definitions are used, unless otherwise described. Halo is fluoro, chloro, bromo, or iodo. Alkyl, alkoxy, aralkyl, alkylaryl, etc. denote both straight and branched alkyl groups; but reference to an individual radical such as "propyl" embraces only the straight chain radical, a branched chain isomer such as "isopropyl" being specifically referred to. Aryl includes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of nonperoxide oxygen, sulfur, and N(X) wherein X is absent or is H, O, ($C_1$–$C_4$) alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The term "amino acid ester" encompasses the product of the reaction of a hydroxy group with the carboxy group of an N-protected amino acid, optionally following by removal of the protecting group. Useful amino acids include the "protein amino acids" and the di- and tri-peptides thereof listed on page 391 of Remington's Pharmaceutical Sciences (18th ed.). These esters can be prepared by the procedures of H. Han et al., Pharmaceutical Res., 15, 1154 (1998).

Some compounds may exhibit polymorphism. It is to be understood that the present invention encompasses any racemic, optically active, polymorphic, or stereoisomeric form, or mixtures thereof, of a compound of the invention, which possess the useful properties described herein, it being well known in the art how to prepare optically active forms (for example, by resolution of the racemic form by recrystallization techniques, or enzymatic techniques, by synthesis from optically active starting materials, by chiral synthesis, or by chromatographic separation using a chiral stationary phase) and how to determine adenosine agonist activity using the tests described herein, or using other similar tests which are well known in the art.

Specific and preferred values listed below for radicals, substituents, and ranges, are for illustration only; they do not exclude other defined values or other values within defined ranges for the radicals and substituents.

Specifically, $C_1$–$C_7$ alkyl can be methyl, ethyl, propyl, isopropyl, butyl, isobutyl, sec-butyl, pentyl, 3-pentyl, hexyl or heptyl; ($C_3$–$C_6$) cycloalkyl can be cyclopropyl, cyclobutyl, cyclopentyl, or cyclohexyl; ($C_3$–$C_6$)cycloalkyl ($C_1$–$C_6$)alkyl can be cyclopropylmethyl, cyclobutylmethyl, cyclopentylmethyl, cyclohexylmethyl; 2-cyclopropylethyl, 2-cyclobutylethyl, 2-cyclopentylethyl, or 2-cyclohexylethyl.

As used herein, the term "cycloalkyl" encompasses bicycloalkyl, (norbornyl, 2.2.2-bicyclooctyl, etc.) and tricycloalkyl (adamantyl, etc.), optionally comprising 1–2 NH, O or S.

($C_1$–$C_4$) alkoxy can be methoxy, ethoxy, propoxy, isopropoxy, butoxy, isobutoxy, sec- or butoxy, ($C_2$–$C_4$) alkenyl can be vinyl, allyl, 1-propenyl, 2-propenyl, 1-butenyl, 2-butenyl, 3-butenyl, ($C_2$–$C_6$)alkanoyl can be acetyl, propanoyl, butanoyl or pentanoyl; halo($C_1$–$C_7$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl, hydroxy($C_1$–$C_6$) alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; ($C_1$–$C_4$)alkoxycarbonyl ($CO_2R^3$) can be methoxycarbonyl, ethoxycarbonyl, propoxycarbonyl, isopropoxycarbonyl, or butoxycarbonyl; ($C_1$–$C_4$)alkylthio can be methylthio, ethylthio, propylthio, isopropylthio, butylthio, or isobutylthio; ($C_2$–$C_6$)alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazolyl, pyraxolyl, pyrrolyl, pyrazinyl, tetrazolyl, pyridyl (or its N-oxide), thienyl, pyrimidinyl (or its N-oxide), indolyl, isoquinolyl (or its N-oxide) or quinolyl (or its N-oxide).

A specific value for X is amino, monomethylamino or dimethylamino.

A specific value for $R^1$ is carboxy($C_1$–$C_7$)alkyl, ($C_1$–$C_4$)alkoxycarbonyl($C_1$–$C_7$)alkyl, 3-N-pyridylpropyloxycarbonyl($C_1$–$C_7$)alkyl; or 3-hydroxypropyloxycarbonyl($C_1$–$C_7$alkyl, and the 3-α-amino acid esters thereof.

Preferably, $C_1$–$C_7$ alkyl in $R^1$ is —$CH_2CH_2CH_2$—.

A specific value for Y is the L-valine or L-glycine ester.

A specific value for $R^2$ is H, methyl, ethyl, propyl or phenyl.

Compounds of formula (I) can be synthesized by the procedures of J. A. Baker et al., J. Chem, Soc. (c), 2478 (1970), and modified by the general procedures set forth in U.S. Pat. Nos. 5,843,943 and 5,877,180.

Preferred compounds of formula (I) and then syntheses are depicted below on Table 1 and in Schemes 1–4.

TABLE 1

Ester Derivatives

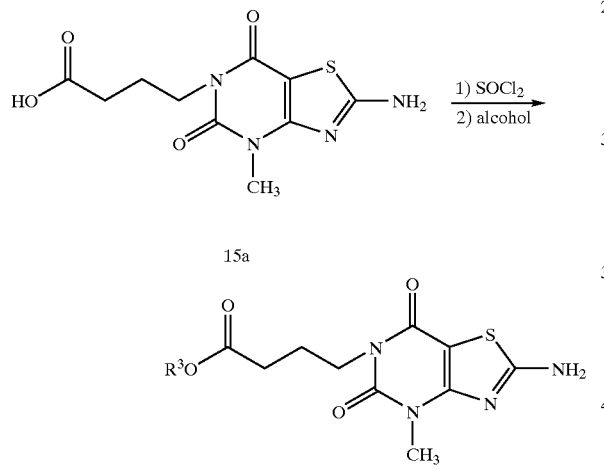

15a

TABLE 1-continued

| alcohol | ester | TNF inhib. ($IC_{50}$) |
|---|---|---|
| EtOH | ethyl 8a | 676 nM |
| HO-CH₂CH₂CH₂-pyridine | pyridinylpropyl 1I-183 | 1.3 μM |
| isopropyl-OH | isopropyl 1I-189 | — |
| HO-t-Bu | ter-butyl 1I-190 | — |
| HO-CH₂CH₂CH₂-OH | hydroxypropyl 1I-191 | — |

Scheme 1
L-Valine prodrug

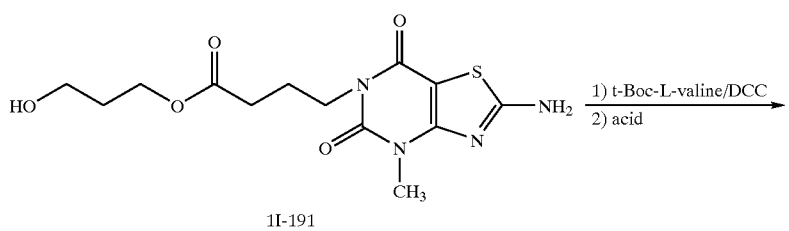

1I-191

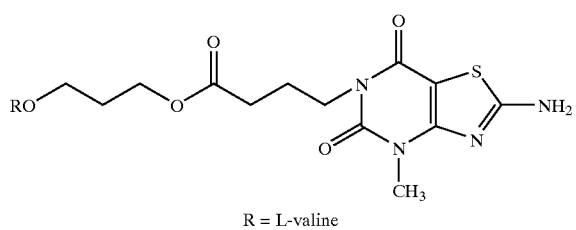

R = L-valine

Scheme 2
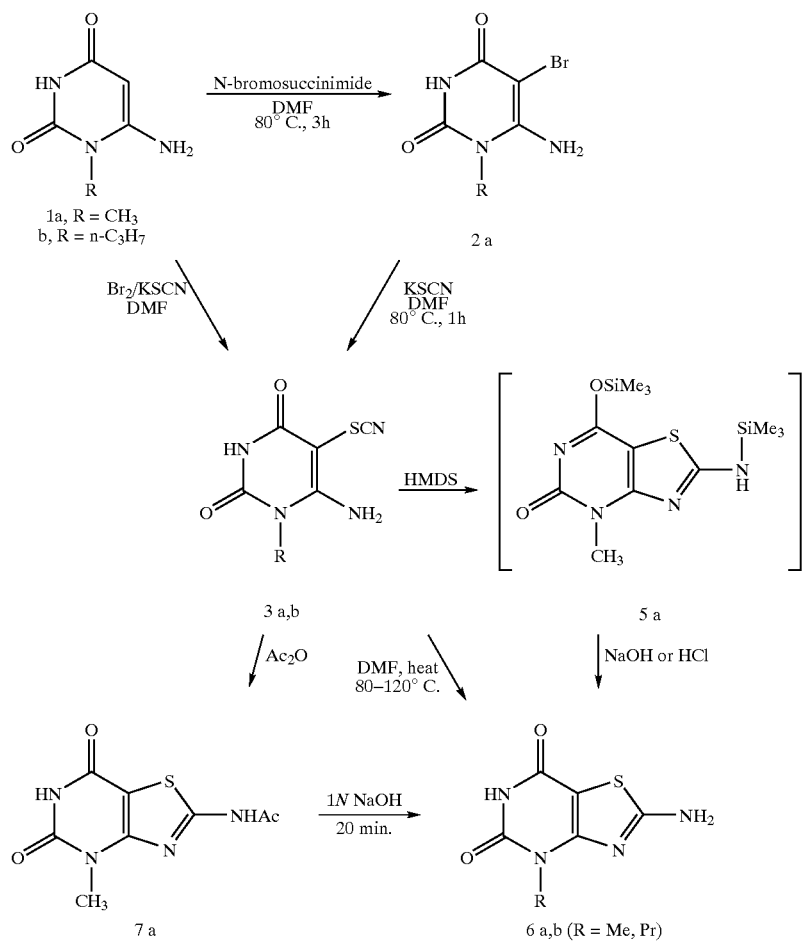
Scheme 3
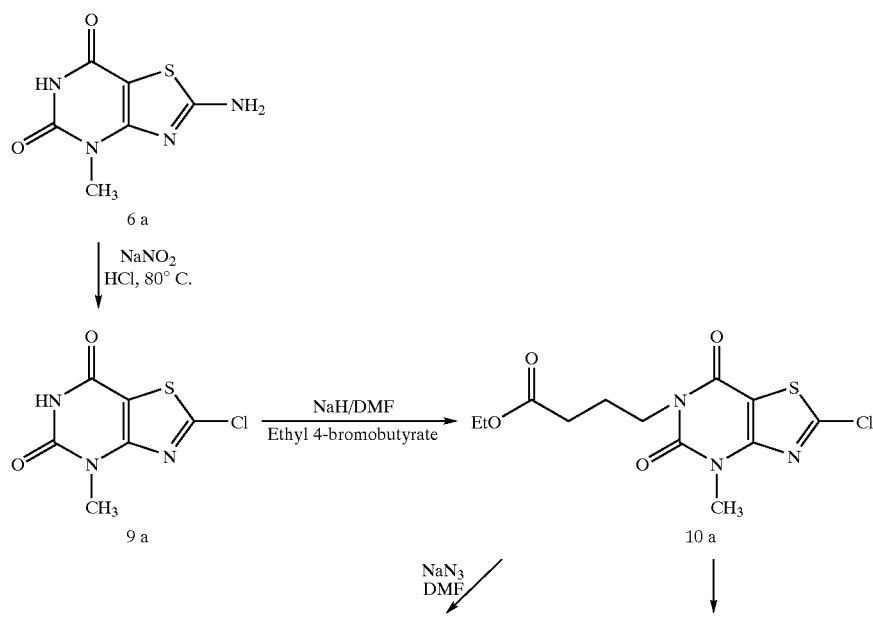

-continued
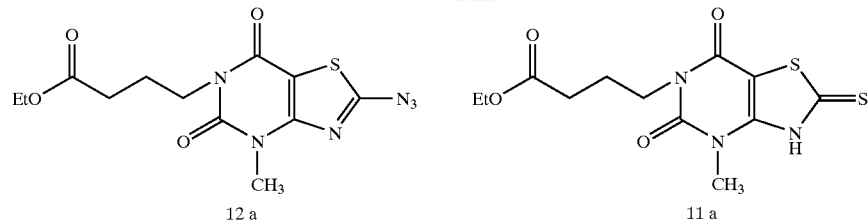
12 a          11 a
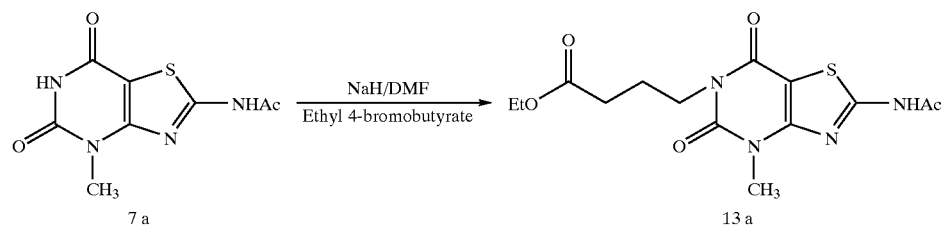
7 a          13 a
Scheme 4
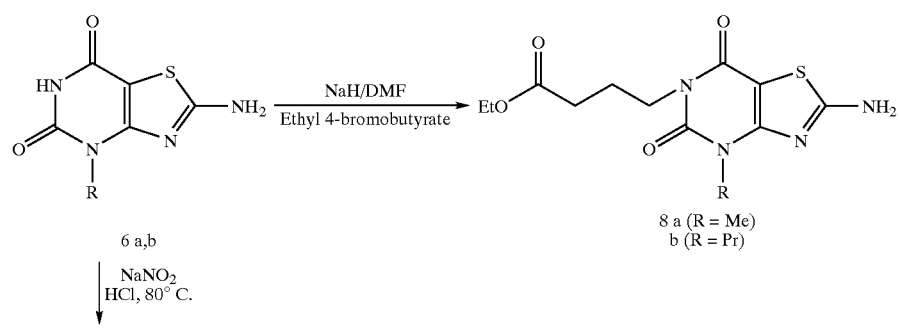
6 a,b          8 a (R = Me)
b (R = Pr)
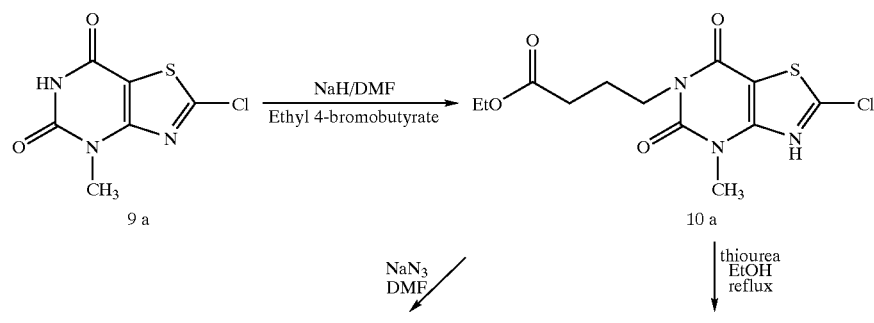
9 a          10 a
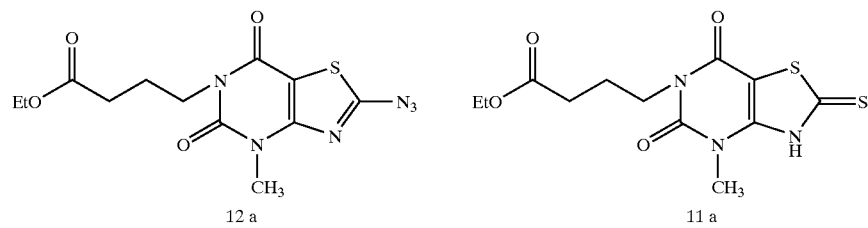
12 a          11 a

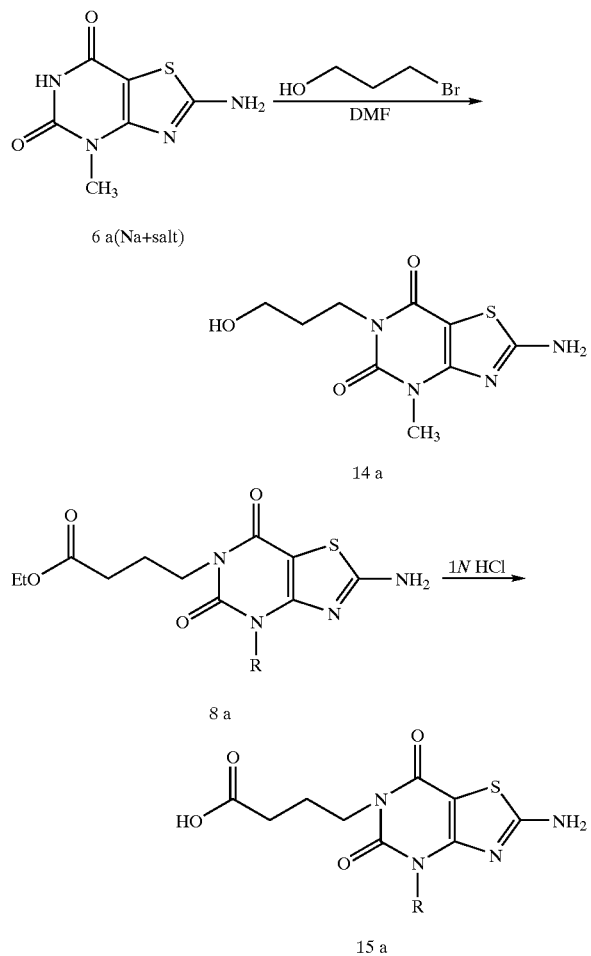

Scheme 5

6 a(Na+salt)

14 a 8 a 15 a

Examples of pharmaceutically acceptable salts of compounds of formula (I) are organic acid addition salts formed with acids which form a physiological acceptable anion, for example, tosylate, methanesulfonate, malate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example, calcium) salts of carboxylic acids can also be made.

The compounds of formula (I) can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compounds may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparations of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid composition can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula (I) to the skin are disclosed in Jacquet et al. (U.S. Pat. No. 4,608,392), Geria (U.S. Pat. No. 4,992,478), Smith et al., (U.S. Pat. No. 4,559,157) and Wortzman (U.S. Pat. No. 4,820,508).

Dosages of the compounds of the invention will vary depending on the age, weight and presenting condition of the host to be treated, as well as the potency of the particular compound administered. Such variables will be readily be accounted for by those of ordinary skill in the clinical art. In particular, dosages will be adjusted upward or downward for each recipient based on the severity of the condition to be treated and accessibility of the target cells to the pharmaceutical formulations of the invention. Where possible, it will be preferable to administer the pharmaceutical formulations of the invention locally at the site of the target cells; e.g., onto inflamed skin or by infusion to another organ of the host. Thus, dosages will also vary depending on the route of administration and the extent to which the formulations of the invention are expected to reach target cells before dilution or clearance of the formulation.

Generally, based on experience with other inhibitors of intracellular responses to external stimuli (such as pentoxifylline) and the data provided herein, good results can be expected to be achieved in an adult host of about 60 kg body weight in a dosage range of about 250 to about 4,000 mg/day, preferably between about 1,000 and about 3,500 mg/day (i.e., a "therapeutically effective dosage"). These dosages may be combined with other conventional pharmaceutical therapies for inflammation and fibrosis; e.g., administration of non-steroidal anti-inflammatory medications.

The compounds of the invention vary in potency. Those of ordinary skill in the art will recognize that lesser or greater dosages of the compounds of the invention may be required depending on the potency of the particular compound being administered. Useful dosages of the compounds of formula (I) can be determined by comparing their in vitro activity, and in vivo activity in animal models. Methods for the extrapolation of effective dosages in mice, and other animals, to humans are known to the art; for example, see U.S. Pat. No. 4,938,949.

Those of ordinary skill in the art will be familiar with means to develop analogues to the compounds specifically described herein which, although not structurally identical thereto, possess the same biological activity. Such compounds are within the scope of the invention and may be identified according to the protocols described below and in the examples.

Through exposure of cells to the compounds of the invention under controlled conditions, the responsiveness of cells to inflammatory agents and intracellular mechanisms therefor can be investigated. This information will not only better elucidate the intracellular pathways responsible for cellular responses to particular stimuli, but will also aid in the identification of anti-inflammatory and anti-fibrosis therapeutic compounds.

To identify and select therapeutic compounds for use in treating conditions such as inflammation and fibrosis, cells (or intracellular components such as microsomes) which have not been exposed to an inflammatory or fibroblast proliferation inducing agent (e.g., LPS, TNFα, IL-1, PDGF) are exposed to such an agent and the candidate therapeutic compound. Specifically, a control group of cells is incubated with a known amount of the inflammatory or fibroblast proliferation inducing agent. Treatment groups of cells are exposed to the same amount of inflammatory or fibroblast proliferation inducing agent as well as aliquots of the candidate therapeutic compound. Inflammatory responses or fibroblast proliferation in each group are detected by conventional means known to those of skill in the art (such as the assay steps described in the examples) and compared.

To identify and select therapeutic compounds for use in treating conditions of cell senescence or apoptosis, cells (or intracellular components such as microsomes) which have not been exposed to a senescence or apoptosis inducing agent (e.g., cytokines such as TNFα and exogenous stimuli such as heat, radiation and chemical agents), are exposed to such an agent and to the candidate therapeutic compound. Inhibition of senescence or apoptosis is measured as a function of cell growth. Those of ordinary skill in the art will be familiar with techniques for obtaining such measurements, examples of which are provided below.

"Therapeutically effective compounds" will be those which, when administered according to the invention and sound medical practices, provide cells with protection against inflammation-associated conditions compared to control values for cellular reactions to a preselected inducing agent.

The invention having been fully described, examples illustrating its practice are set forth below. These examples should not, however, be considered to limit the scope of the invention, which is defined by the appended claims.

In the examples, the abbreviation "min." refers to minutes, "hrs" and "h" refer to hours, and measurement units (such as "ml") are referred to by standard abbreviations. "mp" refers to melting point.

EXAMPLE 1

6-Amino-5-bromo-1-methyluracil (2a)

A mixture of 6-amino-1-methyluracil (14.0 g, 100 mmol), N-bromosuccinimide (21.0 g, 118 mmol), and dry DMF (250 mL) was heated at 80° C. for 3 h. The reaction mixture was evaporated in vacuo and the residue was slurried with ice-cold 50% aqueous ethanol (150 mL) and filtered. The resulting off-white solid was washed with ethanol, then ether and dried to yield 18.0 g 2a (83%). mp 274° C. dec; UV pH 1 $\lambda$max 276 nm; NMR $\delta$ (DMSO-$d_6$) 3.26 (s, 3H, $CH_3$), 7.02 (s, 2H, $NH_2$), 10.89 (s, 1H, NH).

EXAMPLE 2

2-Amino-4-methylthiazolo[4,5-d]pyrimidine-5,7-dione Sodium salt (6a)

A mixture of compound 1I-160 (14.0 g, 64 mmol), potassium thiocyanate (14.0 g, 144 mmol) and DMF (250 mL) was heated at 80° C. for 2 h and filtered hot to remove inorganics. The filtrate was evaporated to dryness in vacuo and hexamethyldisilazane (200 mL) was added and the mixture heated at 130° C. for 30 min. The salmon-colored solid did not dissolve but ammonia was given off indicating some silylation occurred. The HMDS was decanted from the solid and 1N NaOH (150 mL) was added. The mixture was heated to near boiling for a few minutes whereupon the solid nearly dissolved and then the mixture became very thick again. The mixture was cooled on ice, triturated with ice-cold 50% aqueous ethanol and filtered. The solid was washed with cold ethanol, then ether and dried over $P_2O_5$ to yield 13.7 g. The crude product may be recrystallized from 1N NaOH to provide off-white microneedles of the sodium salt of 6a mp>320° C.; UV pH 1 $\lambda$max 223 nm ($\epsilon$ 13,400), 309 (8,100); pH 7 $\lambda$max 223 nm ($\epsilon$17,100), 309 (10,500) pH 11 $\lambda$max 218 nm ($\epsilon$ 17,500), 304 (8,800); NMR $\delta$ (DMSO-$d_6$ 3.33 (s, 3H, $CH_3$), 8.50 (s, 2H, NH2), 11.05 (br s, residual NH).

EXAMPLE 3

Ethyl 4-[2-Amino-4-methyl-5,7-dioxothiazolo [4,5-d]pyrimidin-6-yl]-butanoate (8a)

To a mixture of compound 1I-173 (10.0 g, 45 mmol) and potassium carbonate (3.0 g) in dry DMF (200 mL) at 75° C. was added ethyl 4-bromobutyrate (6.7 mL, 50 mmol) in one lot by syringe. The mixture was stirred at 75° C. for 2 h, evaporated to dryness and the residue was partitioned between water (100 mL) and ethyl acetate (150 mL). The water layer was extracted with EtOAc (2×75 mL) and the combined organic layer was dried over magnesium sulfate, filtered and evaporated onto silica gel (40 mL of 70–230 mesh silica gel 60). Flash column chromatography (5×20 cm, 200–400 mesh) using 5% MeOH/$CH_2Cl_2$ gave 7.0 g (50%) of 8a as a yellow solid. mp 170–171° C.; UV pH 1, 7, 11 $\lambda$max 224 nm ($\epsilon$26,300), 309 (16,400); NMR $\delta$ (DMSO-$d_6$) 1.1 (t, 3H, terminal methyl of ethyl ester), 1.8 (m, 2H, C-3 methylene of butanoate), 2.3 (t, 2H, C-2 methylene), 3.4 (s, 3H, N-4 methyl), 3.8 (t, 2H, C-4 methylene), 4.0 (q, 2H, methylene of ethyl ester), 8.55 (s, 2H, amino).

EXAMPLE 4

Inhibition of TNFα Production by the Compounds of the Invention

Peripheral blood mononuclear cells were isolated from normal human blood on Hypaque-Ficoll density gradients. 100 μl aliquots of monocytes were placed onto 96 well microtiter plates at a density of $5\times10^6$ cells/well in RPMI-1640 medium containing 10% autologous plasma. After incubation for 24 hrs., various concentrations of the test compound in DMSO were added to the plated cells in a volume of 100 μl and incubated for 1 hr. After incubation, 10 μg/ml of LPS was added to each well.

Eighteen hours after exposure of the plated cells to LPS, 100 μl of medium was collected from each well and assayed (by ELISA, R&D Systems) for release of IL-1 and TNFα, using recombinant human TNF as a standard (n=5). The sensitivity of the assay ranged from 10–100 pg/ml.

FIG. 1 depicts the effect of compounds 8b, 8a, rolipram and SB-210313 on TNFα production. Rolipram is an inhibitor of phosphodiesterase-4, and has been reported to be a potent inhibitor of human TNFα production. SB-210313 is an inhibitor of the p38 mitogen activated protein kinase, which was developed at Smith Kline Beecham, and has been reported to be a potent inhibitor of TNFα synthesis. 8b ($IC_{50}$=421 nM) and 8a ($IC_{50}$=676 nM) are more potent than rolipram ($IC_{50}$=2500 nM) or SB-210313 ($IC_{50}$=1146 nM).

Figure 2:
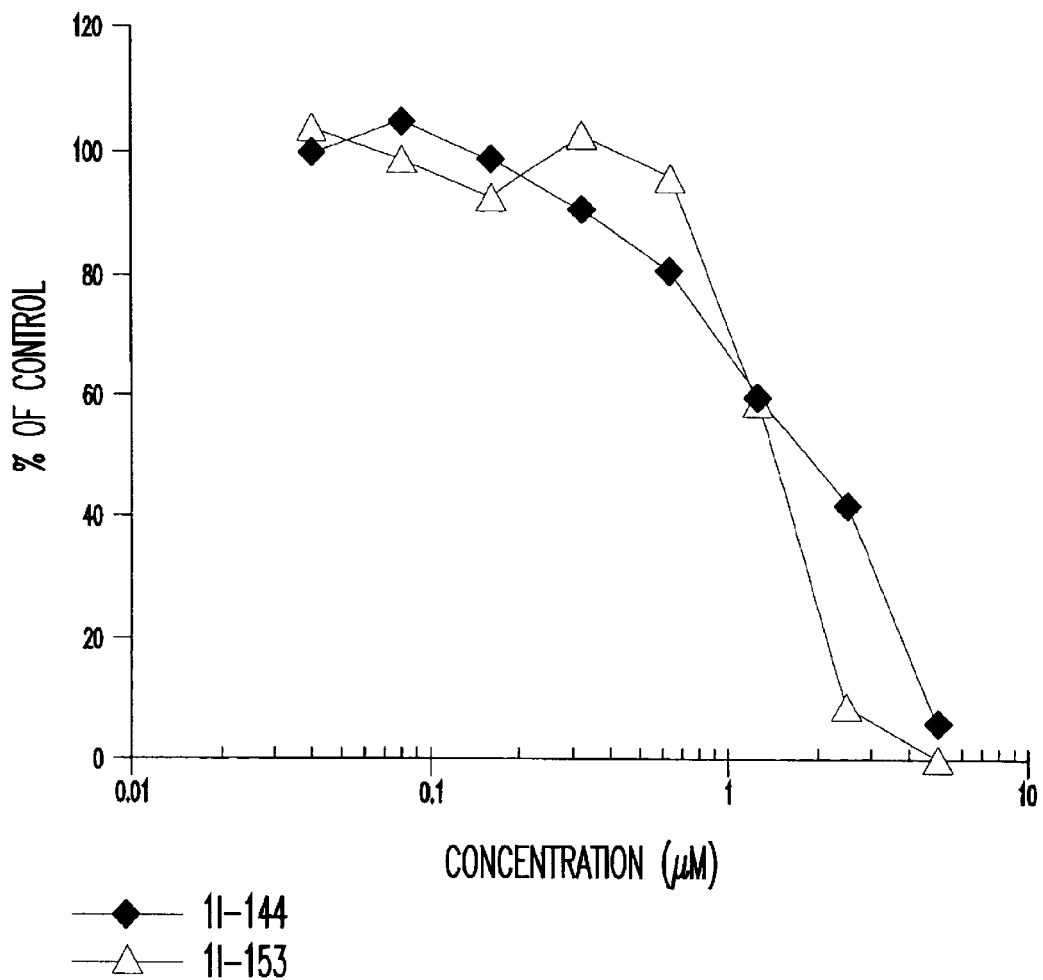
FIG. 2 is a graph depicting the effect of 8b and 8a on IL-1B production in human monocytes using ELISA.
Figure 3:
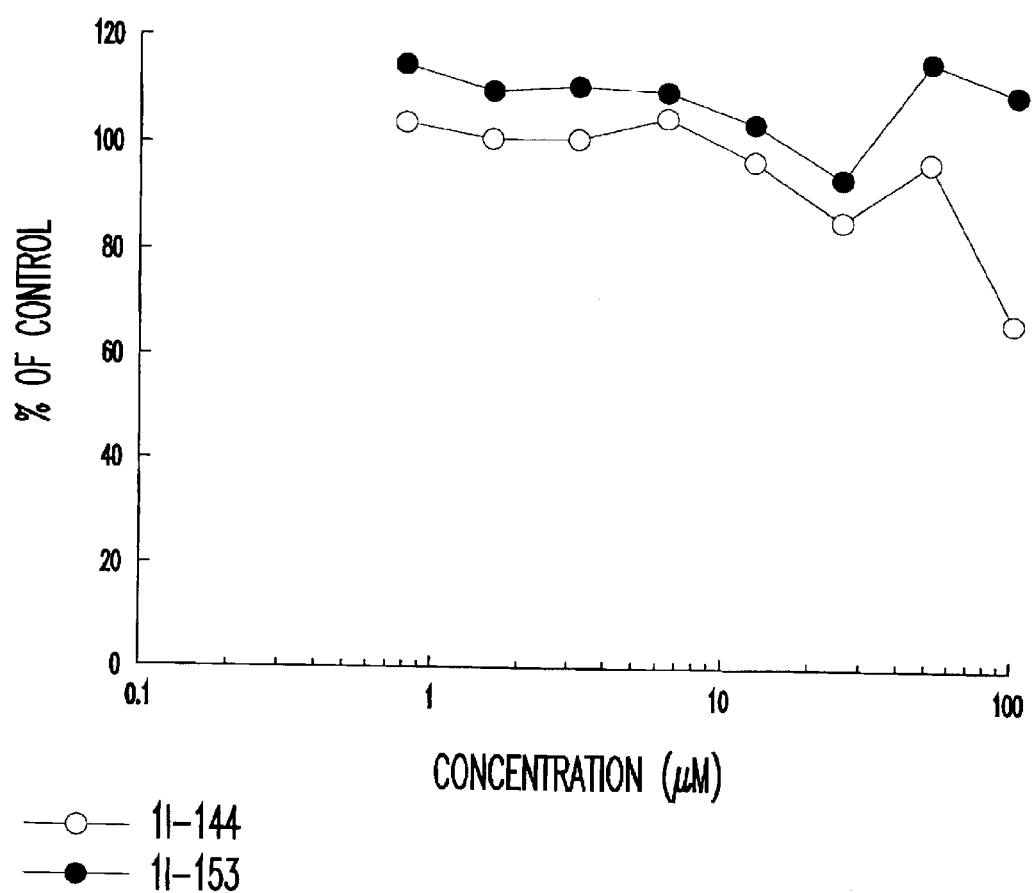
FIG. 3 is a graph depicting the effect of 8a and 8b on Jurkat cell growth using the MTT assay.

FIG. 2 summarizes the effects of 8b and 8a on the production of IL-1β by human monocytes stimulated with LPS, under the same conditions used for the TNFα study. Both compounds 8b and 8a also inhibit IL-1 production with a 50% inhibitory dose of about 1–3 μM.

EXAMPLE 5

Effect of 8a and 8b on Jurkat Cell Growth

In this experiment, cells of the continuous human lymphoblastoid Jurkat cell line were suspended at $1\times10^5$/ml in complete medium containing various amounts of 8a and 8b dissolved in DMSO. Seventy-two hours later the cell density was assessed using the MTT assay, which measures the reduction of a tetrazolium dye. The cell densities were compared to control cultures lacking any additional drugs. Note that neither 8b nor 8a had significant growth inhibitory activity at a concentration below 50 μM.

EXAMPLE 6

Inhibition of Phosphodiesterase IV Activity by Compounds of the Invention

Figure 4:
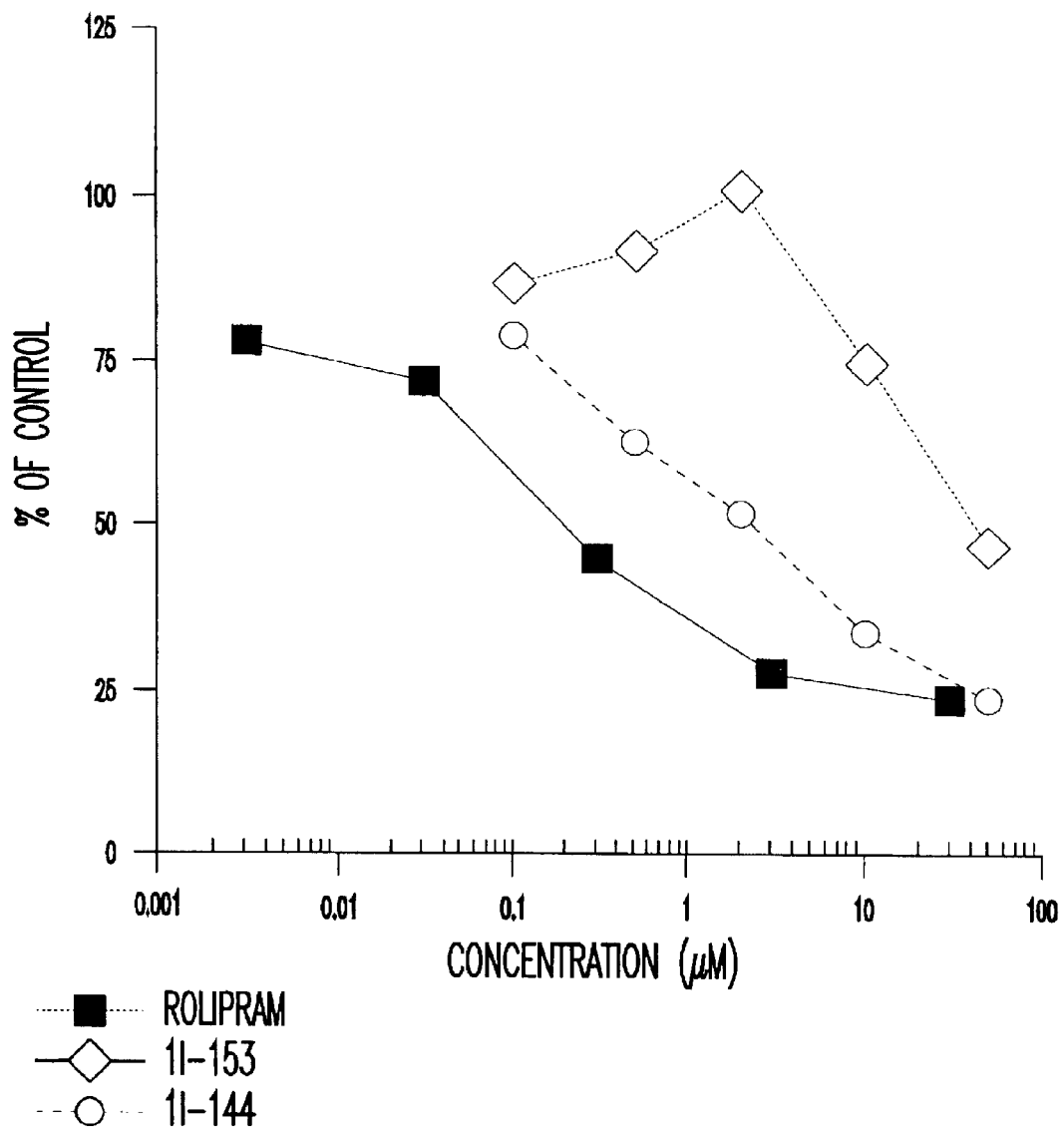
FIG. 4 is a graph depicting the activity of compounds of the invention as Type IV PDE inhibitors vs. rolipram in the U937 cell extract.

Phosphodiesterase type 4 is a target for inhibitors of TNFα synthesis such as rolipram. Therefore, the effects of 8b and 8a on the PDE4 enzyme purified from the U937 human monocyte cell line were evaluated. Extractions of this cell line were separated on a Sephadex column and the rolipram inhibitable fractions were isolated. PDE4 was assayed by a commercial radioassay that measures the conversion of $^3$H-cyclic AMP to AMP and subsequently to adenosine, as assessed by ion exchange chromatography. The reaction was started with the addition of PDE and incubated at 37° C. for 10 minutes, then terminated by boiling for 2 minutes. After completion of the reaction, 5'-nucleotidase (Sigma) was added to convert all AMP to adenosine. Then a Dowex®-I slurry was added to absorb the negatively charged [$^3$H]-cAMP. 500 μl of 0.1 M HEPES/0.1 M NaCl (pH 8.5) was added to each tube, then the reaction mixture was applied to the column. Unreacted cAMP was washed off with Hepes/NaCl and the reaction mixture eluted with acetic acid. Recovery was determined with the [$^{34}$C]-AMP As shown in FIG. 4, the test compound rolipram inhibited PDE4 with an $IC_{50}$ of 196 nm. In contrast, the $IC_{50}$ values for 8a were 43 μM and 2.1 μM, respectively. These values contrast strongly with the potencies of the compounds as inhibitors of TNFα synthesis. This experiment rules out the possibility that 8a and 8b act principally by inhibition of PDE4.

EXAMPLE 7

Acute Toxicity Testing

ICR mice (ca. 20 g) were injected IP for 5 days with 50 mg/kg, and 100 mg/kg of each of 8a and 8b dispersed in aqueous hydroxypropyl β-cyclodextrin (50% w/v). Five daily IP injections at 100 mg/kg produced no weight change or detectable lethargy in the mice over 30 days of observation.

EXAMPLE 8

In Vivo Effects of Orally Administered 8a

Figure 5:
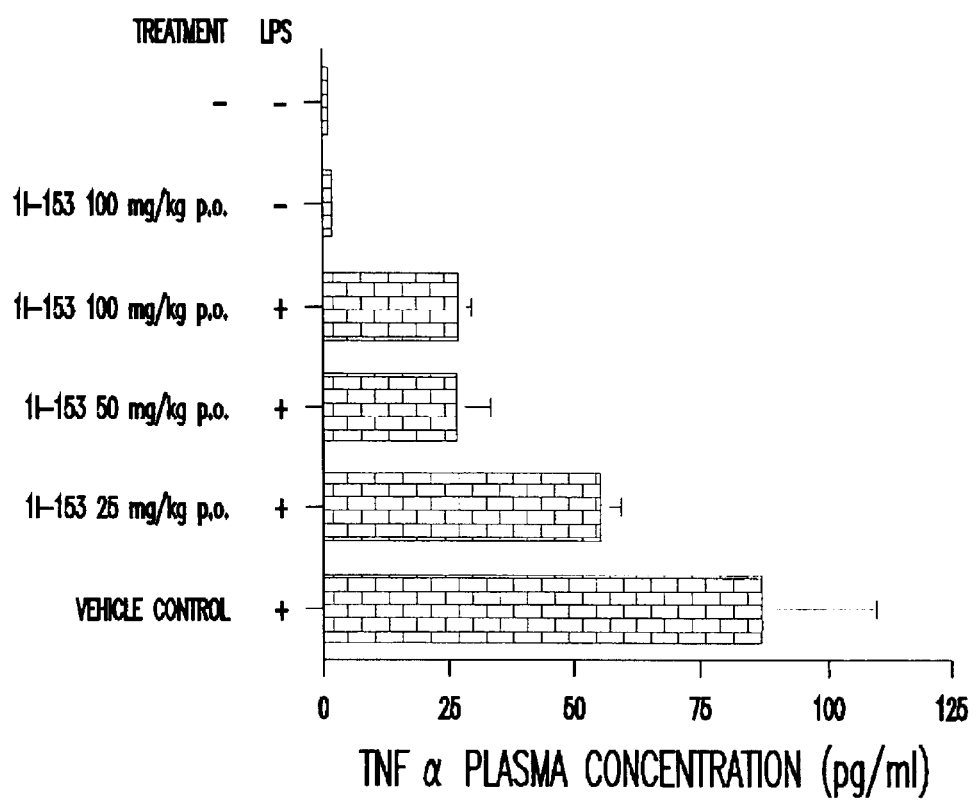
FIG. 5 is a graph depicting the 8a dose response on LPS-induced TNFα stimulation.

ICR mice were dosed orally at 25, 50 and 100 mg/kg of 8a in cyclodextrin, prepared as in Example 7. After 1 hr., each mouse was injected with *E. coli* LPS (1 μg/mouse). Two hours later, 250 μl samples of blood were obtained by retro-orbital bleeding without anesthetization. The blood was heparinized, centrifuged for 10 min. at 10 K rpm (4° C.) and TNFα determined by ELISA. As shown in FIG. 5, even 25 mg/kg of 8a had a significant inhibitory effect on TNFα plasma concentration, which was greater at 50 mg/kg. The two bars at the top of the figure show the baseline levels of TNFα in the mouse plasma, which were undetectable, and the effects of 8a administered alone, which were negligible.

EXAMPLE 9

Time Course Study of TNFα Inhibition

Figure 6:
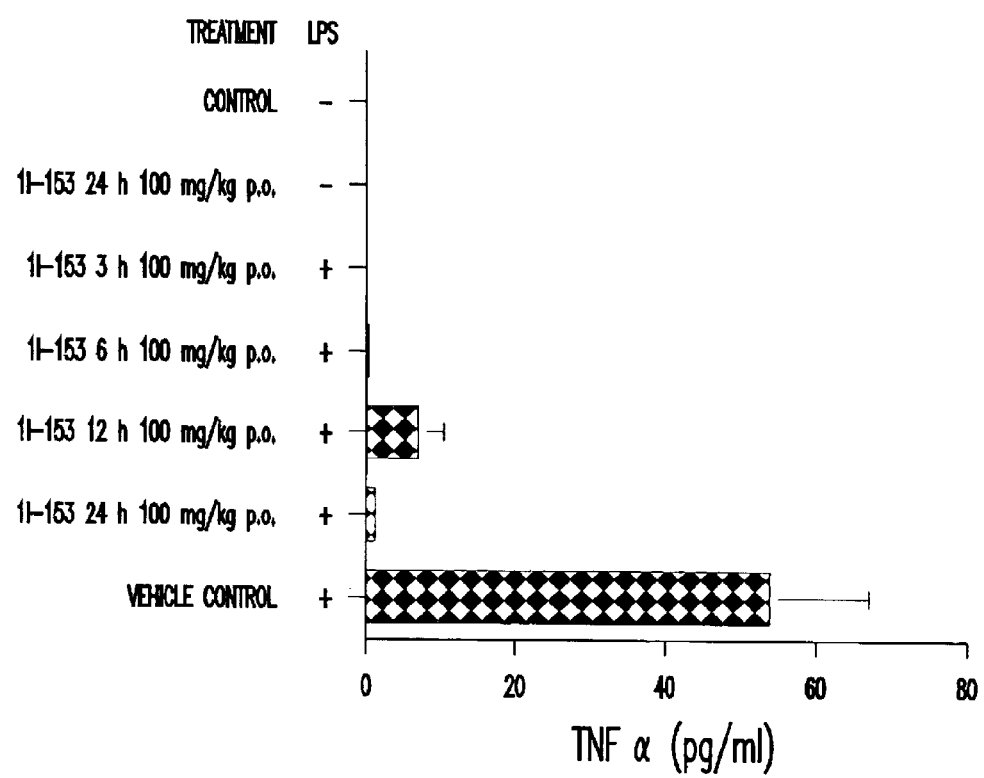
FIG. 6 is a graph depicting the 8a time course on LPS-induced acute inflammation.

The purpose of these experiments was to determine how long after administration of compound 8a by gavage could its inhibitory effects on LPS-induced TNFα production be detected. Accordingly, all the ICR in this instance were given 8a at a dosage of 100 mg/kg by gavage. Then at 1, 4, 10, and 24 hours later, each animal received 1 μg/ml IP LPS, and two hours later (i.e., at 3, 6, 12, and 26 hours), blood was removed for TNFα ELISA. As shown in FIG. 6, even after 24 hours, 8a at this high dosage completely inhibited the accumulation of TNFα in the plasma of LPS-injected mice. These experiments demonstrate that 8a is orally active, and has a relatively long biological effect in vivo.

EXAMPLE 10

Inhibition of Adjuvant Arthritis

Since TNFα antagonists have shown considerable value in the treatment of rheumatoid arthritis, compound 8a was evaluated in an animal model that is TNFα dependent. Adjuvant arthritis is an acute inflammatory disease induced in certain rat strains by the administration of heat-killed mycobacteria dispersed in incomplete Freund's adjuvant. The disease is manifest by severe joint swelling, mainly of the ankles and feet.

Figure 7:
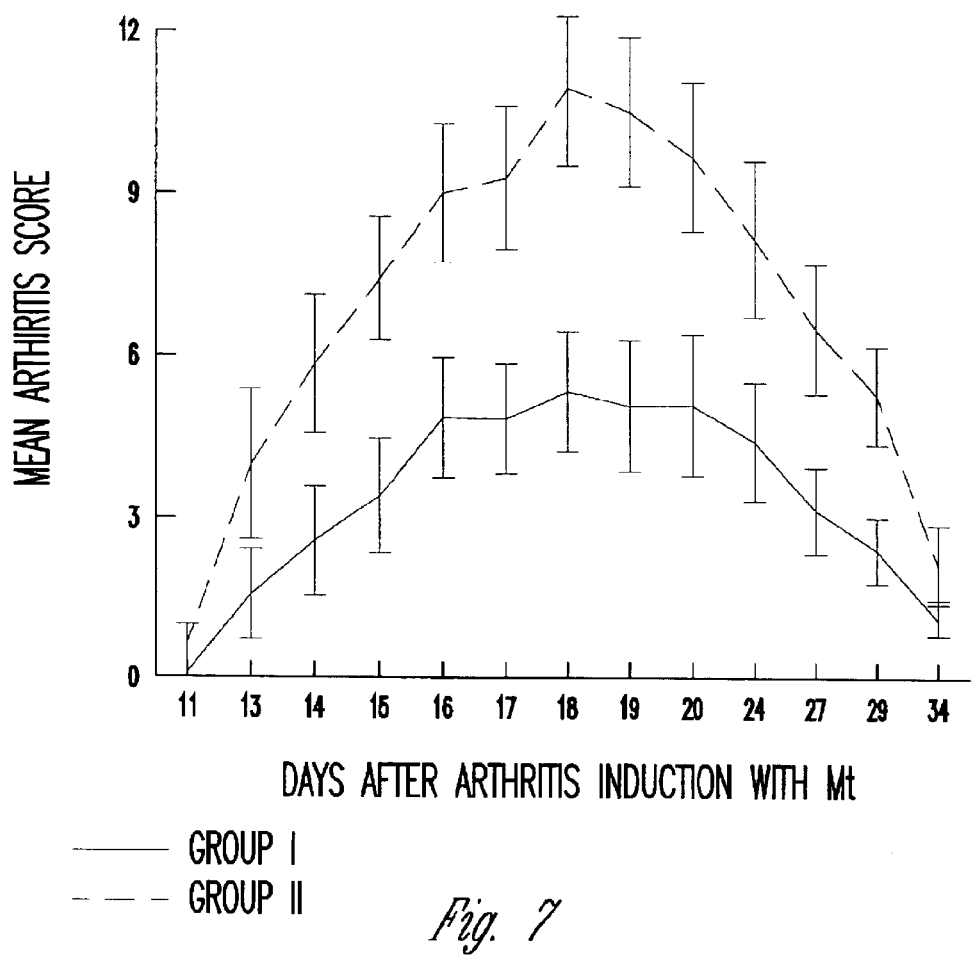
FIG. 7 depicts the arthritis scores of untreated mice and mice treated with 8a over time.

Two groups of seven Lewis rats each were immunized intradermally with mg of heat-killed mycobacterium tuberculosis emulsified in incomplete Freund's adjuvant. One day later, one group of animals (N=7) received 100 mg/kg of 8a by gavage. Another group of animals received no treatment. The oral dosing was continued every day up to day 30. The clinical scores of the animals were determined every other day at day 14 by an observer who did not know which group had been treated. The results are shown in FIG. 7. The mean arthritis score can vary from 0 to 4 for each limb, yielding a maximum score of 16. Note that the untreated animals (group 1) achieved a mean arthritis score of 10 on day 18. In contrast, the treated animals reach a mean arthritis score of 5, for 50% inhibition. These results are statistically significant at the p<0.05 level.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

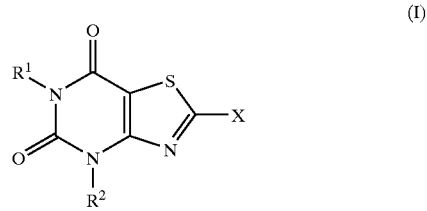

wherein $R^1$ is -Z-A wherein Z is (a) $C_1$–$C_7$ alkyl, optionally interrupted with 1–2 double bonds, 1–2 nonperoxide O, or 1–2 NR wherein R is individually H, phenyl, benzyl, $C_2$–$C_4$ alkanoyl or $C_1$–$C_6$ alkyl; (b) $C_3$–$C_6$ cycloalkyl; (c) $C_3$–$C_6$ cycloalkyl $C_1$–$C_3$ alkyl; (d) $C_6$–$C_{10}$ aryl; or (e) $C_6$–$C_{10}$ aryl $C_1$–$C_3$ alkyl;

A is N(R)$_2$, C$_2$–C$_4$ acyloxy, SO$_3$H, PO$_4$H$_2$, N(NO)(OH), SO$_2$NH$_2$, PO(OH)NH$_2$, OH, SO$_2$R$^3$, tetrazolyl, or COOR$^3$ wherein R$^3$ is H, phenyl, benzyl or C$_1$–C$_6$ alkyl optionally substituted with 1–2 OR, heteroaryl, C$_6$–C$_{10}$ aryl, C$_2$–C$_4$ alkenyl, phenyl, tetrazolyl or an amino acid residue formed by the removal of a hydrogen atom from the —COOH group of an amino acid;

R$^2$ is a C$_1$–C$_6$ alkyl, C$_2$–C$_4$ alkenyl, C$_6$–C$_{10}$ aryl C$_1$–C$_2$ alkyl or C$_6$–C$_{10}$ heteroaryl C$_1$–C$_2$ alkyl;

X is H, halo, OR, SR, N$_3$ or N(R)$_2$; or a pharmaceutically acceptable salt thereof.

2. The compound of claim 1 wherein Z is (C$_2$–C$_6$)alkyl or phenyl.

3. The compound of claim 1 or 2 wherein A is CO$_2$R$^3$.

4. The compound of claim 3 wherein R$^3$ is H or (C$_1$–C$_6$) alkyl, optionally substituted with OH, C$_6$–C$_{10}$ heteroaryl or the amino acid residue.

5. The compound of claim 4 wherein the amino acid is an L-valine residue or L-glycine residue.

6. The compound of claim 4 wherein R$^3$ is (C$_1$–C$_6$)alkyl substituted with 4-pyridyl.

7. The compound of claim 1 or 2 wherein -Z-A is ethoxycarbonylpropyl.

8. The compound of claim 1 or 2 wherein X is NH$_2$.

9. The compound of claim 1 or 2 wherein R$^2$ is CH$_3$ or CH$_2$CH$_2$CH$_3$.

10. A pharmaceutical composition comprising the compound of claim 1 in combination with a pharmaceutically acceptable carrier.

11. The compound of claim 1 having the formula:

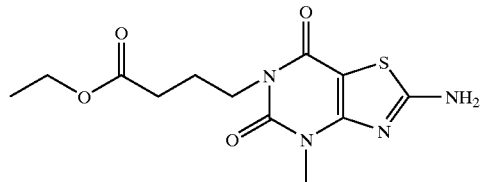

or a pharmaceutically acceptable salt thereof.

12. The compound of claim 1 having the formula:

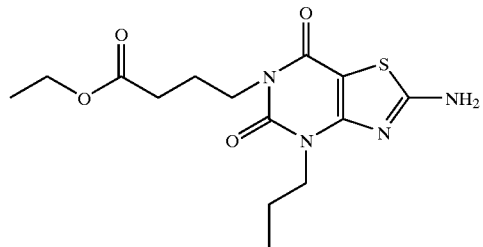

or a pharmaceutically acceptable salt thereof.

* * * * *

UNITED STATES PATENT AND TRADEMARK OFFICE
CERTIFICATE OF CORRECTION

PATENT NO. : 6,930,101 B1
DATED : August 16, 2005
INVENTOR(S) : Carson et al.

It is certified that error appears in the above-identified patent and that said Letters Patent is hereby corrected as shown below:

Title page,
Item [56], References Cited, OTHER PUBLICATIONS,
"Benjamin K. Gill" reference, delete "/L10K.html" and insert -- /1L10K.html --.
"Goncalves de Morales et al." reference, delete "Morales" and insert -- Moraes --; delete "Effects" and insert -- Effect --; and after "lung." insert -- Brit. --.
"Mbagwu, G. O.," reference (second occurrence), after "G.O.," insert -- et al., --.
"Mizuno, Y., et al.," reference, delete "Ribofuransoyl" and insert -- Ribofuranosyl --.
"Nagahara, K., et al.," reference, delete "[4 5-d]" and insert -- [4,5-d] --; and delete "ad" and insert -- as --.
"Sen, D., et al.," reference, delete "Microl." and insert -- Microbiol. --.
"Boujrad, N., et al.," reference, delete "Hormones-Stimulated" and insert -- Hormone-Stimulated --.
"Burrows, J.L.," reference, delete "Automted" and insert -- Automated --.
"Cifone, M.G., et al.," reference, delete "Signalling" and insert -- Signaling --; and delete "(FAS/Apo-1)" and insert -- (Fas/Apo-1) --.
"Cottam, H.B., et al.," reference, delete "Compunds" and insert -- Compounds --.
"Dressler, K.A., et al.," reference, delete "Sphinomyelin Siganl" and insert -- Sphingomyelin Signal --.
"Han, H., et al.," reference, delete "Phamaceutical" and insert -- Pharmaceutical --.
"Joseph, C.K., et al.," reference, delete "Cermaide" and insert -- Ceramide --.
"Liu, M.K., et al.," reference, delete "Kinase" and insert -- Kinases --.
"Lozano, J., et al.," reference, delete "$^k$B-dependent" and insert -- kB-dependent --.
"Marshall, P.J., et al.," reference, delete "Pyrroliomidazole" and insert -- Pyrroloimidazole --.
"Moreira, R., et al.," reference, delete "Penicillan" and insert -- Penicillin --.
"Nishigaki, S., et al.," reference, delete "Heterocyles" and insert -- Heterocycles --.
"Rivas, C.I., et al.," reference, delete "Signalling" and insert -- Signaling --.
"Sliwa, K., et al.," reference, delete "Perfomance" and insert -- Performance --.
"Wu, J., et al.," reference, delete "Signalling" and insert -- Signaling --.

Column 1,
Line 31, delete "Infect, Dis., 2" and insert -- Infect. Dis., 9 --.
Line 67, delete "3, 2" and insert -- 35, 2 --.

Column 2,
Line 5, delete "$A_1$, and $A_2$," and insert -- $A_1$ and $A_{2a}$ --.
Line 18, delete "(1)" and insert -- (I) --.
Line 43, after "Y" insert -- is --.

UNITED STATES PATENT AND TRADEMARK OFFICE
CERTIFICATE OF CORRECTION

PATENT NO. : 6,930,101 B1
DATED : August 16, 2005
INVENTOR(S) : Carson et al.

It is certified that error appears in the above-identified patent and that said Letters Patent is hereby corrected as shown below:

Column 3,
Line 13, delete "(1)" and insert -- (I) --.

Column 5,
Line 6, delete "$(C_1-C_7 alkyl$" and insert -- $(C_1-C_7)alkyl$ --.

Column 11,
Line 10, delete "6a(Na+salt)" and insert -- 6a($Na^+$ salt) --.

Column 17,
Line 25, delete "[$^{34}C$]" and insert -- [$^{14}C$] --.

Column 18,
Line 26, after "with" insert -- 5 --.

Signed and Sealed this

Seventeenth Day of January, 2006

JON W. DUDAS
*Director of the United States Patent and Trademark Office*